United States Patent
Biedermann et al.

[11] Patent Number: 5,672,176
[45] Date of Patent: Sep. 30, 1997

[54] ANCHORING MEMBER

[76] Inventors: Lutz Biedermann, Am Schäfersteig 8, D-78048 VS-Villingen; Jürgen Harms, D-Maximilianstr. 5, D-76133 Karlsruhe, both of Germany

[21] Appl. No.: 611,991

[22] Filed: Mar. 5, 1996

[30] Foreign Application Priority Data

Mar. 15, 1995 [DE] Germany .................. 195 09 332.1

[51] Int. Cl.⁶ .................................................. A61B 17/70
[52] U.S. Cl. .................................. 606/61; 606/72; 606/65
[58] Field of Search ............................. 606/61, 65, 72, 606/73

[56] References Cited

U.S. PATENT DOCUMENTS

| | | | |
|---|---|---|---|
| 5,207,678 | 5/1993 | Harms et al. | 606/61 |
| 5,443,567 | 8/1995 | Biedermann et al. | 606/65 |

FOREIGN PATENT DOCUMENTS

| | | |
|---|---|---|
| 0 382 256 A1 | 8/1990 | European Pat. Off. . |
| 43 07 576 C1 | 4/1994 | Germany . |
| WO 91/01115 | 2/1991 | WIPO . |
| WO 94/00066 | 1/1994 | WIPO . |

*Primary Examiner*—Michael Buiz
*Assistant Examiner*—Daphna Shai
*Attorney, Agent, or Firm*—George W. Neuner

[57] ABSTRACT

An anchoring member for connecting a rod with a bone comprises a screw member having a treaded portion and a screw head with a spherical segment-shaped portion, a seat part receiving said screw head of said screw member and said rod, and a pressure member formed to embrace said screw head from its side opposite to said threaded portion. The seat part has a first end, a second end opposite to said first end, an axis of symmetry passing through said first and second end and a bore which is coaxial with said axis of symmetry for passing said threaded portion therethrough and has a first portion adjacent to said first end, said first portion having a substantially U-shaped cross-section with two free legs with an internal screw thread for receiving said rod therebetween. The seat part further has a second portion adjacent to said second end, said second portion tapering towards the second end with a predetermined cone angle, and a pressure member has an outer conical surface in a region laterally surrounding said screw head, said conical surface tapering towards said second end with a cone angle corresponding to said predetermined cone angle.

12 Claims, 1 Drawing Sheet

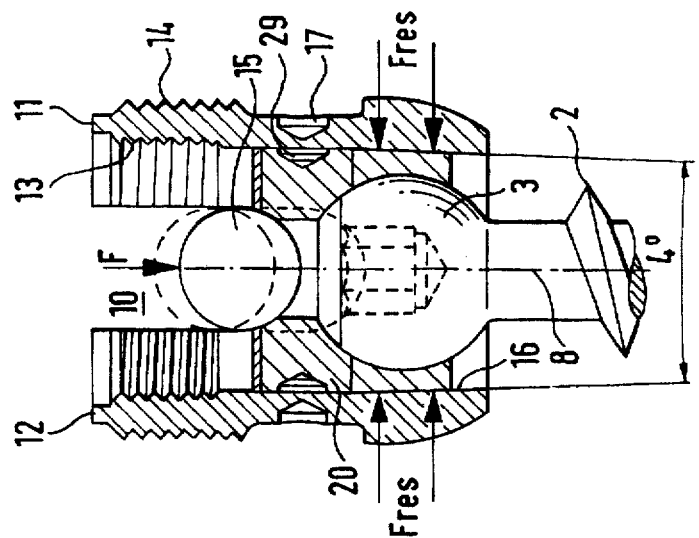
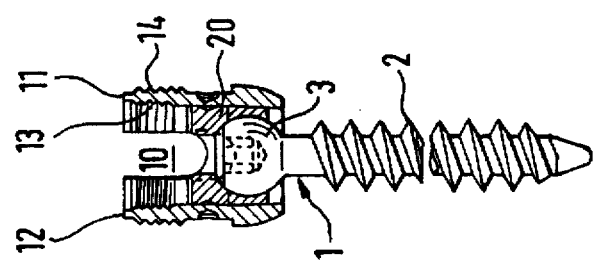
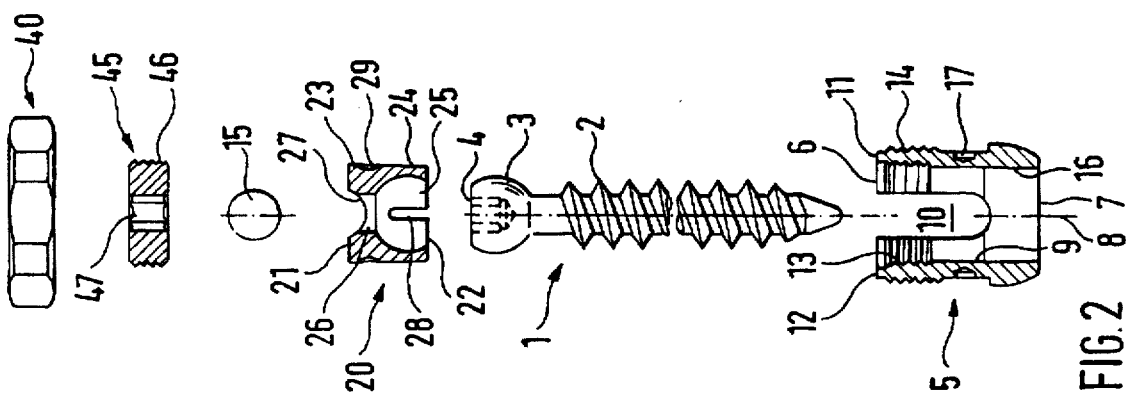

ANCHORING MEMBER

BACKGROUND OF THE INVENTION

The invention relates to an anchoring member for connecting rod with a bone.

Such an anchoring member formed as a polyaxial bone screw is disclosed in the German patent 43 07 576. With this device the position of the screw member relative to the seat part is fixed by a pressure disk which acts upon the head of the screw member and which is urged against the screw of the screw member by an inserted correction rod and a rod locking screw. This creates the problem that when loosening the rod locking screw for relative positioning of rod and anchoring member the lock of the head of the screw member with respect to the seat part is simultaneously released. Thus, each time the position of the seat part on the rod connecting the vertebrae is readjusted the seat part is also moved with respect to the head of the screw member which is disadvantageous.

OBJECTS OF THE INVENTION

It is an object of the invention to provide an improved anchoring member whereby the above-mentioned drawbacks are avoided. It is a further object to provide an anchoring member which keeps the screw head of the screw member locked to the seat part when adjusting the position of the seat part relative to the rod.

SUMMARY OF THE INVENTION

In order to achieve the above-mentioned objects the invention provides an anchoring member for connecting a rod with a bone, the anchoring member comprising a screw member having a threaded portion and a screw head with a spherical segment-shaped portion, a seat part receiving the screw head and the rod, the seat part having a first end, a second end opposite to the first end, an axis of symmetry passing through the first and second end, a bore which is coaxial with the axis of symmetry for passing the threaded portion therethrough, and has a first portion adjacent to the first end, the first portion having a substantially U-shaped cross-section with two free legs with an internal screw thread for receiving the rod therebetween and a second portion adjacent to the second end, a second portion tapering towards the second end with a predetermined cone angle, and a pressure member formed to embrace the screw head from its side opposite to its threaded portion and having an outer conical surface in a region laterally surrounding the screw head, the conical surface tapering towards the second end with a cone angle corresponding to the predetermined cone angle.

BRIEF DESCRIPTION OF THE DRAWINGS

Further features and advantages of the invention will be apparent from the description of embodiments with reference to the figures. In the figures:

FIG. 1 shows a cross-section of the anchoring member with a rod to be placed therein, partly in sectional representation;

FIG. 2 shows the anchoring member in detail and exploded representation; and

FIG. 3 is a partly sectional representation of the anchoring member with inserted screw member and pressure member.

DESCRIPTION OF A PREFERRED EMBODIMENT

As best shown in the FIGS. 2 and 3 an anchoring member comprises the proper screw member 1 having a threaded shaft 2 and a head 3. The head 3 is formed as a spherical segment in the region adjacent to the threaded shaft 2. The length of the head 3 in axial direction is larger than the radius of the head. The head 3 has a recess 4 for engagement with a hexogen socket screw key at its face opposite to the threaded shaft 2 and coaxially therewith.

The anchoring member further comprises a seat part 5 for receiving the head 3 of the screw member 1. The seat part 5 comprises a first end 6 and an opposite second end 7 as well as an axis of symmetry 8 passing through the first and second end. A bore 9 is coaxial with the axis of symmetry for passing the threaded shaft therethrough in direction from the first end. In a first region adjacent to the first end 6 the seat part 5 has a U-shaped recess 10 which is symmetric with respect to the axis of symmetry 8, the recess 10 having a base directed towards the second end 7 and two free lateral legs 11, 12 extending towards the first end 6. In the region of the legs 11, 12 the bore is cylindrical and the seat part has an internal screw thread 13 and an external screw thread 14. The channel formed by the U-shaped recess 10 has a size just enough to fit a rod 15 therein connecting a plurality of such anchoring members. At a second region adjacent to the second end 7 the cylindrical portion of the bore 9 is followed by a portion 16 tapering towards the second end 7 with a cone angle of about 4°. The axial length of this portion 16 corresponds substantially to the axial dimensions of the head 3.

At the second end the diameter of the bore 9 is considerably larger than that of the threaded shaft whereby the latter can be pivoted, when in an inserted state, around the axis of symmetry 8 within a cone angle.

A pressure member 20 acting upon the head 3 of the screw member and having a first face 21 away from the head 3 and an opposite second face 22 is provided for locating the position of the head 3 within the seat part 5. Adjacent to the first face 21 the pressure member has a substantially cylindrical first portion 23 having an outer diameter selected so as to allow an axial sliding motion of the pressure member within the bore 9 of the seat part 5. The pressure member 20 further comprises a second portion 24 adjacent to the first portion 23 and to the second face 22. The second portion 24 has an outer surface conically tapering towards the second face 22 with a cone angle corresponding to that of the portion 16 of the bore 9 within the seat part 5. A spherical segment shaped recess 25 for receiving the head 3 is formed coaxially at the second face 22 and opens towards the second end 22. The spherical segment shaped recess 25 has a radius which substantially corresponds to the radius of the head 3. The axial extension of the recess 25 is larger than the radius thereof. The wall of the pressure member 20 has four slits arranged therein in a peripherally equidistant manner and parallel to the axis, the slits opening towards the second face 22 and having an axial length which is larger than the radius of the recess 25.

The pressure member 20 further comprises, in its cylindrical first portion 23, a bore 26 providing a passage for a screwing tool engaging the recess 4. The bore 26 is coaxial with the cylinder axis and joins the recess 25. A recess 27 having the shape of a cylinder portion and extending perpendicular to the cylinder axis of the first portion 23 is formed in the surface of the pressure member at the first face 21 thereof. The center of curvature is on the axis of symmetry. The depth of the recess is not larger than the radius of the recess. The radius of curvature of the recess 27 corresponds to the radius of curvature of the base of the U-shaped recess 10 of the seat part 5. The longitudinal slits 28 surve the purpose to bend up the conicial portion 24 of the pressure member embracing the head 3 so that the spherical segment shaped recess 25 of the pressure member 20 can be pushed onto the head 3 of the screw.

Countersinks 29 extending perpendicular to the axis of symmetry are provided opposite to each other on the jacket of the pressure member 20. Corresponding crimp bores 17 are formed in the jacket of the seat part 5.

Further, a member embracing the outside of the two lateral legs 11, 12 is provided. The member is formed as a swivel nut 40 for locating the rod 15 to be received and has an internal screw thread corresponding to the external screw thread 14 at the two legs of the seat part 5. Moreover, there is a locking member 45 formed as a threaded screw. The locking member 45 has an external screw thread 46 cooperating with the internal screw thread 13 of the legs 11, 12 for screwing the locking member into the U-shaped recess 10 of the seat part 5. The locking member 45 further has a hexagon recess 47 for engagement of a screwing tool.

All components of the described enchoring member are made of a physically friendly material, in particular of titanium.

For preparation the pressure member 20 is first pushed onto the head 3 so that the head is embraced by the edge of the spherical segment shaped recess 25. The forces generated when pushing on act to slightly bend apart the pressure member at the longitudinal slits 28 so that the screw head 3 can be inserted into the spherical segment shaped recess 25 and the pressure member snaps onto the head 3. The positive connection between the edge of the spherical segment shaped recess 25 and the screw head 3 can be obtained by a following slight compression of the pressure member.

The threaded shaft 2 is then inserted into the seat part from the first end 6 thereof until the conical outer surface of the second portion 24 of the pressure member 20 frictionally engages the wall of the conical portion 16 of the bore 9. In the course of this the pressure member 20 is turned so that the axis of the partial cylindrical recess 27 is exactly in the plane of symmetry of the U-shaped channel 10 of the seat part 5. This position is locked by slight crimping by means of the crimp bores 17, 29 without impeding a sufficient movement of the pressure member 20 in direction of the axis of symmetry 8 of the seat part.

In operation the screw member is screwed in and the rod 15 is then placed into the seat part 5 by insertion from the outside into the U-shaped recess 10. After adjusting the desired position of the anchoring member relative to the rod 15, the rod is firmly clamped by tightening the swivel nut 40. As shown in particular in FIG. 1, tightening of the swivel nut 40 causes a force F to be exerted through the rod 15 onto the pressure member 20 in direction of the axis of symmetry 8 so that the pressure member 20 is pressed into the seat part together with the screw head 3 to completely push the conical second portion 24 of the pressure member 20 into the conical portion 16 of the bore 9 of the seat part.

If the entire conical surfaces of the second portion 24 of the pressure member sit close to the surfaces of the bore 9 of the seat part, the seat part exverts, as in particular shown in FIG. 1, a force Fres onto the pressure member in a radial direction with respect to the axis of symmetry 8 which blocks a movement of the screw head within the recess 25 even if the swivel nut 40 is loosened for readjusting the position of the rod 15 relative to the seat part 5. Thus, the angular position of the screw member 1 relative to the seat part 5 remains as fixed during the preceding lock of the rod.

Since the cone angle is selected to cause self-locking of the formed connection between the conical surface of the portion 16 of the bore and the portion 24 of the pressure member, this connection cannot loosen on its own. Rather, an additional external force of considerable extent is necessary to surmount the frictional force acting to prevent loosening.

In operation a corresponding anchoring member is arranged in each of the plurality of adjacent segments of a spinal column, whereby a precise adjustment is made segment after segment for adjusting the engagement position of the individual anchoring members at the rod relative to the longitudinal axis of the rod. For precisely adjusting the position of the seat part relative to the rod the swivel nut 40 can again be loosened because when adjusting the position of the screw head within the seat part for making a primary adjustment of the position of the seat part relative to the rod, the pressure member is firmly pressed into the seat part 5 and thereby locks the position of the screw head 3 which lock cannot be released in normal operation due to the self-locking action.

After the position of the seat part 5 relative to the rod 15 as obtained by precise adjustment has been determined the swivel nut is again tightened. Thereupon, the locking member 45 is screwed in between the legs 11, 12 in direction towards the rod for locking the swivel nut.

Preferably, the above-described cone angle is in a range between 2° and 10°. Particular preferred is a range of between 2° and 5° for this angle.

Although the invention has been described with reference to a specific example embodiment, it is to be understood that it is intended to cover all modifications and equivalences within the spirit and scope of the appended claims.

What is claimed is:

1. An anchoring member for connecting a rod with a bone, said anchoring member comprising a screw member having a threaded portion and a screw head with a spherical segment-shaped portion, a seat part receiving said screw head and said rod, said seat part having a first end, a second end opposite to said first end, an axis of symmetry passing through said first and second ends, a bore which is coaxial with said axis of symmetry for passing said threaded portion therethrough and has a first portion adjacent to said first end, said first portion having a substantially U-shaped cross-section with two free legs with an internal screw thread for receiving said rod therebetween, and a second portion adjacent to said second end, said second portion tapering towards said second end with a predetermined cone angle, and a pressure member formed to embrace said screw head from its side opposite to said threaded portion and having an outer conical surface in a region laterally surrounding said screw head, said conical surface tapering towards said second end with a cone angle corresponding to said predetermined cone angle.

2. The anchoring member of claim 1, said predetermined cone angle being in the range of from about 2° to approximately 10°.

3. The anchoring member of claim 1, the cone angle being about 4°.

4. The anchoring member of claim 1, wherein said pressure member has a first face and an opposite second face, a substantially cylindrical first portion adjacent to said first face having an outer diameter sized for a sliding fit of said pressure member within said bore, and a second portion adjacent to said first portion, said second portion being formed as a trancated cone having an outer surface which conically tapers towards said second face.

5. The anchoring member of claim 4, comprising a first recess formed within said second portion of said pressure member for receiving said screw head, said first recess being shaped as a spherical segment and opening towards said second face.

6. The anchoring member of claim 5, comprising a bore formed in said pressure member for passing a screwing tool therethrough into engagement with said screw head, said bore being coaxial with a cylinder axis of said first portion and joining said first recess.

7. The anchoring member of claim 5, comprising a plurality of longitudinal slits formed in said pressure member, said slits having a longitudinal axis extending parallel to the axis of said first portion and being open towards said second face.

8. The anchoring member of claim 7, comprising two opposite longitudinal slits each having a longitudinal axis, the two longitudinal axes lying in a plane passing through the cylinder axis of said first cylindrical portion and extending perpendicular to said cylinder axis of said second recess, said longitudinal slits extending closely to said first face of said pressure member.

9. The anchoring member according to claim 5, wherein said first recess has a depth in axial direction and a radius, said depth being greater than said radius.

10. The anchoring member of claim 1, comprising a second recess formed in said pressure member on the side thereof opposite to said screw head, said second recess having the shape of a cylinder portion with an axis extending perpendicular to said axis of symmetry and having a radius of a curvature which corresponds to a radius of curvature formed at a base of said U-shaped first portion defined by said two legs.

11. The anchoring member of claim 1, comprising crimp means for securing said pressure member with said screw head therein against rotation within said seat part.

12. The anchoring member of claim 1, comprising a swivel nut member embracing said two free legs on the outside thereof, said legs having an external screw thread and said swivel nut member having an internal screw thread cooperating with said external screw thread, and a locking member for locking said swivel nut member, said locking member having an external screw thread and said legs having an internal screw thread engaging said external screw thread of said locking member.

\* \* \* \* \*

UNITED STATES PATENT AND TRADEMARK OFFICE
CERTIFICATE OF CORRECTION

PATENT NO. : 5,672,176
DATED : September 30, 1997
INVENTOR(S) : Lutz Biedermann and Jurgen Harms It is certified that error appears in the above-identified patent and that said Letters Patent is hereby corrected as shown below:

On title page,

[56] References Cited replace 5,443,567 with 5,443,467

Signed and Sealed this

Twenty-fourth Day of March, 1998

Attest:

BRUCE LEHMAN

Attesting Officer        Commissioner of Patents and Trademarks